(12) United States Patent
Dotson et al.

(10) Patent No.: US 9,592,405 B2
(45) Date of Patent: *Mar. 14, 2017

(54) OPHTHALMIC PHOTOTHERAPY DEVICE AND ASSOCIATED TREATMENT METHOD

(71) Applicant: Photospectra Health Sciences, Inc., Toronto (CA)

(72) Inventors: Robert S Dotson, Bainbridge Island, WA (US); Graham Merry, Toronto (CA)

(73) Assignee: PHOTOSPECTRA HEALTH SCIENCES, INC., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/050,483

(22) Filed: Feb. 23, 2016

(65) Prior Publication Data

US 2016/0166849 A1 Jun. 16, 2016

Related U.S. Application Data

(63) Continuation of application No. 13/679,557, filed on Nov. 16, 2012, now abandoned, which is a
(Continued)

(51) Int. Cl.
*A61N 5/06* (2006.01)
*A61F 9/008* (2006.01)
(Continued)

(52) U.S. Cl.
CPC .......... *A61N 5/0613* (2013.01); *A61B 3/0025* (2013.01); *A61B 3/102* (2013.01);
(Continued)

(58) Field of Classification Search
CPC ... A61N 5/0613; A61F 9/008; A61F 9/00821; A61F 2009/00872
(Continued)

(56) References Cited

U.S. PATENT DOCUMENTS 4,917,486 A * 4/1990 Raven ................. A61F 9/00821
351/221
4,930,504 A 6/1990 Diamantopoulos et al.
(Continued)

FOREIGN PATENT DOCUMENTS

EP 2 532 747 A1 12/2012
WO 2004/105873 A1 12/2004
(Continued)

OTHER PUBLICATIONS

Begum et al., "Treatment with 670 nm Light Up Regulates Cytochrome C Oxidase Expression and Reduces Inflammation in an Age-Related Macular Degeneration Model," *PLoS ONE* 8(2), e57828, 2013. (11 pages).
(Continued)

*Primary Examiner* — William Thomson
*Assistant Examiner* — John Downey
(74) *Attorney, Agent, or Firm* — Seed IP Law Group LLP

(57) ABSTRACT

An ophthalmic phototherapy device and associated phototherapy treatment method for promoting healing of damaged or diseased eye tissue. The ophthalmic phototherapy device includes a light emitting mechanism for transmitting light of at least one preselected wavelength to the eye tissue. The ophthalmic phototherapy method includes directing light of at least one wavelength for a selected period of time to a portion of damaged or diseased eye tissue, whereby the light transmitted to the damaged or diseased eye tissue stimulates cellular activity in the eye tissue to promote healing.

32 Claims, 9 Drawing Sheets

Related U.S. Application Data continuation-in-part of application No. 12/172,697, filed on Jul. 14, 2008, now abandoned, which is a continuation-in-part of application No. 11/858,351, filed on Sep. 20, 2007, now Pat. No. 7,479,136, which is a continuation-in-part of application No. 11/106,416, filed on Apr. 14, 2005, now abandoned.

(51) Int. Cl.

| | | |
|---|---|---|
| A61F 9/007 | (2006.01) | |
| A61B 3/00 | (2006.01) | |
| A61B 3/10 | (2006.01) | |
| A61B 3/12 | (2006.01) | |
| A61F 9/00 | (2006.01) | |
| A61B 5/00 | (2006.01) | |

(52) U.S. Cl.
CPC .......... *A61B 3/1241* (2013.01); *A61B 5/0071* (2013.01); *A61B 5/7282* (2013.01); *A61F 9/00* (2013.01); *A61F 9/008* (2013.01); *A61F 9/0079* (2013.01); *A61N 5/0622* (2013.01); *A61F 2009/00868* (2013.01); *A61F 2009/00872* (2013.01); *A61F 2009/00891* (2013.01); *A61N 2005/0643* (2013.01); *A61N 2005/0644* (2013.01); *A61N 2005/0651* (2013.01); *A61N 2005/0652* (2013.01); *A61N 2005/0659* (2013.01); *A61N 2005/0662* (2013.01); *A61N 2005/0663* (2013.01)

(58) Field of Classification Search
USPC .......................................................... 606/4–6
See application file for complete search history.

(56) References Cited

U.S. PATENT DOCUMENTS

| | | | |
|---|---|---|---|
| 5,259,380 A | 11/1993 | Mendes et al. | |
| 5,290,272 A | 3/1994 | Burstein et al. | |
| 5,520,679 A | 5/1996 | Lin | |
| 5,533,997 A | 7/1996 | Ruiz | |
| 5,683,436 A | 11/1997 | Mendes et al. | |
| 5,755,752 A | 5/1998 | Segal | |
| 5,766,233 A | 6/1998 | Thiberg | |
| 5,904,678 A | 5/1999 | Pop | |
| 5,964,749 A | 10/1999 | Eckhouse et al. | |
| 5,997,141 A * | 12/1999 | Heacock | A61B 3/1225 |
| | | | 351/221 |
| 6,019,754 A | 2/2000 | Kawesch | |
| 6,238,424 B1 | 5/2001 | Thiberg | |
| 6,274,614 B1 | 8/2001 | Richter et al. | |
| 6,283,956 B1 | 9/2001 | McDaniel | |
| 6,287,296 B1 | 9/2001 | Seiler et al. | |
| 6,319,273 B1 * | 11/2001 | Chen | A61N 5/062 |
| | | | 128/898 |
| 6,349,001 B1 | 2/2002 | Spitzer | |
| 6,387,089 B1 | 5/2002 | Kreindel et al. | |
| 6,443,978 B1 | 9/2002 | Zharov | |
| 6,471,716 B1 | 10/2002 | Pecukonis | |
| 6,537,302 B1 | 3/2003 | Thiberg | |
| 6,607,522 B1 | 8/2003 | Hamblin et al. | |
| 6,676,655 B2 | 1/2004 | McDaniel | |
| 6,677,366 B2 | 1/2004 | Richter et al. | |
| 6,689,124 B1 | 2/2004 | Thiberg | |
| 6,811,563 B2 | 11/2004 | Savage, Jr. et al. | |
| 6,887,260 B1 | 5/2005 | McDaniel | |
| 7,014,639 B2 | 3/2006 | Walneck et al. | |
| 7,118,563 B2 | 10/2006 | Weckwerth et al. | |
| 7,303,578 B2 | 12/2007 | De Taboada et al. | |
| 7,309,348 B2 | 12/2007 | Streeter et al. | |
| 7,354,432 B2 | 4/2008 | Eells et al. | |
| 7,479,136 B2 | 1/2009 | Dotson | |
| 7,534,255 B1 | 5/2009 | Streeter et al. | |
| 7,695,504 B2 | 4/2010 | Anders et al. | |
| 7,744,590 B2 | 6/2010 | Eells et al. | |
| 7,914,523 B2 | 3/2011 | Barolet et al. | |
| 7,919,094 B2 | 4/2011 | Schwaeble et al. | |
| 8,025,687 B2 | 9/2011 | Streeter et al. | |
| 8,106,038 B2 | 1/2012 | Margaron et al. | |
| 8,167,921 B2 | 5/2012 | Streeter et al. | |
| 8,308,784 B2 | 11/2012 | Streeter et al. | |
| 8,471,967 B2 | 6/2013 | Miao et al. | |
| 8,508,830 B1 | 8/2013 | Wang | |
| 8,582,209 B1 | 11/2013 | Amirparviz | |
| 8,705,177 B1 | 4/2014 | Miao | |
| 2002/0004673 A1 | 1/2002 | Cho et al. | |
| 2002/0087207 A1 | 7/2002 | Cho et al. | |
| 2002/0198575 A1 * | 12/2002 | Sullivan | A61N 5/0616 |
| | | | 607/88 |
| 2003/0050674 A1 | 3/2003 | Joshi | |
| 2003/0093135 A1 | 5/2003 | Denton et al. | |
| 2004/0002694 A1 * | 1/2004 | Pawlowski | A61F 9/008 |
| | | | 606/4 |
| 2004/0008523 A1 * | 1/2004 | Butler | A61N 5/0613 |
| | | | 362/551 |
| 2004/0116909 A1 * | 6/2004 | Neuberger | A61F 9/008 |
| | | | 606/4 |
| 2004/0193234 A1 * | 9/2004 | Butler | A61N 5/0613 |
| | | | 607/88 |
| 2004/0215293 A1 * | 10/2004 | Eells | A61N 5/0613 |
| | | | 607/89 |
| 2004/0243198 A1 * | 12/2004 | Heacock | A61F 9/008 |
| | | | 607/89 |
| 2005/0055015 A1 * | 3/2005 | Buzawa | A61B 3/135 |
| | | | 606/4 |
| 2005/0159793 A1 | 7/2005 | Streeter | |
| 2006/0184214 A1 | 8/2006 | McDaniel | |
| 2006/0235493 A1 | 10/2006 | Dotson | |
| 2007/0123844 A1 * | 5/2007 | Henry | A61F 9/008 |
| | | | 606/4 |
| 2007/0244526 A1 | 10/2007 | Zaghetto et al. | |
| 2007/0252951 A1 * | 11/2007 | Hammer | A61F 9/008 |
| | | | 351/221 |
| 2008/0009839 A1 | 1/2008 | Dotson | |
| 2008/0009922 A1 * | 1/2008 | Bille | A61F 9/008 |
| | | | 607/89 |
| 2008/0234668 A1 * | 9/2008 | Linnik | A61F 9/0079 |
| | | | 606/4 |
| 2008/0269730 A1 | 10/2008 | Dotson | |
| 2008/0269849 A1 * | 10/2008 | Lewis | A61N 5/0613 |
| | | | 607/91 |
| 2010/0010592 A1 | 1/2010 | De Taboada et al. | |
| 2010/0010594 A1 | 1/2010 | De Taboada et al. | |
| 2010/0016783 A1 | 1/2010 | Bourke, Jr. et al. | |
| 2010/0079356 A1 | 4/2010 | Hoellwarth | |
| 2010/0079865 A1 | 4/2010 | Saarikko et al. | |
| 2013/0009853 A1 | 1/2013 | Hesselink et al. | |
| 2013/0033756 A1 | 2/2013 | Spitzer et al. | |
| 2013/0069985 A1 | 3/2013 | Wong et al. | |
| 2013/0079759 A1 | 3/2013 | Dotson et al. | |
| 2013/0088413 A1 | 4/2013 | Raffle et al. | |
| 2013/0100362 A1 | 4/2013 | Saeedi et al. | |
| 2013/0258270 A1 | 10/2013 | Cazalet et al. | |
| 2014/0171624 A1 | 6/2014 | Krammer et al. | |

FOREIGN PATENT DOCUMENTS

| | | |
|---|---|---|
| WO | 2005/025672 A1 | 3/2005 |
| WO | 2008/009062 A1 | 1/2008 |
| WO | 2012/070054 A1 | 5/2012 |
| WO | 2012/167944 A1 | 12/2012 |
| WO | 2013/062654 A1 | 5/2013 |

OTHER PUBLICATIONS

Belevich et al., "Exploring the proton pump mechanism of cytochrome c oxidase in real time," *Proceedings of the National Academy of Sciences of the United States of America* 104(8):2685-2690, 2007.

(56) References Cited

OTHER PUBLICATIONS

Belevich et al., "Initiation of the proton pump of cytochrome *c* oxidase," *Proceedings of the National Academy of Sciences of the United States of America* 107(43):18469-18474, 2010.

Belevich et al., "Proton-coupled electron transfer drives the proton pump of cytochrome *c* oxidase," *Nature* 440(7085):829-832, 2006.

Brodeur, FLIP4, URL=www.spatrends.com/index, download date Mar. 1, 2005, 1 page.

Chung et al., "The Nuts and Bolts of Low-level Laser (Light) Therapy," *Annals of Biomedical Engineering* 40(2):516-533, 2012.

Damico et al., "New approaches and potential treatments for dry age-related macular degeneration," *Arquivos Brasileiros de Oftalmologia* 75(1):71-75, 2012.

Darlot et al., "Near-Infrared Light Is Neuroprotective in a Monkey Model of Parkinson Disease," *Annals of Neurology* 79(1):59-75, 2016.

De Taboada et al., "Transcranial Laser Therapy Attenuates Amyloid-β Peptide Neuropathology in Amyloid-β Protein Precursor Transgenic Mice," *Journal of Alzheimer's Disease* 23(3):521-535, 2011.

Fells et al., "Mitochondrial signal transduction in accelerated wound and retinal healing by near-infrared light therapy," *Mitochondrion* 4(5-6):559-567, 2004.

Final Office Action, mailed Mar. 12, 2008, for U.S. Appl. No. 11/106,416, Dotson, "Ophthalmic Phototherapy Device and Associated Treatment Method," 8 pages.

Funk et al., "Outer Segments of Retinal Photoreceptors—A Review in the Light of Novel Findings," *Annual Research & Review in Biology* 4(16):2553-2565, 2014. (Abstract Only).

Gkotsi et al., "Recharging mitochondrial batteries in old eyes. Near infra-red increases ATP," *Experimental Eye Research* 122:50-53, 2014.

Gorbikova et al., "The proton donor for O—O bond scission by cytochrome *c* oxidase," *Proceedings of the National Academy of Sciences of the United States of America* 105(31):10733-10737, 2008.

Hashmi et al., "Role of Low-Level Laser Therapy in Neurorehabilitation," *PM&R* 2(12), (Supplement):S292-S305, 2010. (25 pages).

Huang et al., "Biphasic Dose Response in Low Level Light Therapy—An Update," *Dose-Response* 9(4):602-618, 2011.

Huang et al., "Biphasic Dose Response in Low Level Light Therapy," *Dose-Response* 7(4):358-383, 2009.

Huang et al., "Low-level laser therapy (810 nm) protects primary cortical neurons against excitotoxicity in vitro," *Journal of Biophotonics* 7(8):656-664, 2014.

Ivandic et al., "Low-Level Laser Therapy Improves Vision in Patients with Age-Related Macular Degeneration," *Photomedicine and Laser Surgery* 26(3):241-245, 2008.

Jasaitis et al., "Nanosecond electron tunneling between the hemes in cytochrome $bo_3$," *Proceedings of the National Academy of Sciences of the United States of America* 104(52):20811-20814, 2007.

Johnstone et al., "The potential of light therapy in Parkinson's disease," *ChronoPhysiology and Therapy* 4:1-14, 2014.

Johnstone et al., "Turning on Lights to Stop Neurodegeneration: The Potential of Near Infrared Light Therapy in Alzheimer's and Parkinson's Disease," *Frontiers in Neuroscience* 9:Article 500, 2015. (15 pages).

Kaila et al., "Prevention of leak in the proton pump of cytochrome *c* oxidase," *Biochimica et Biophysica Acta* 1777(7-8):890-892, 2008.

Karu et al., "Exact Action Spectra for Cellular Responses Relevant to Phototherapy," *Photomedicine and Laser Surgery* 23(4):355-361, 2005.

Karu, "Mechanisms of Low-Power Laser Light Action on Cellular Level," *Proceedings of SPIE 4159*, 2000. (17 pages).

Laakso et al. (ed.), *Proceedings of the 9th World Association for Laser Therapy Congress*, Foreword and Index, Gold Coast, Australia, Sep. 28-30, 2012, 6 pages.

Lane, "Power Games," *Nature* 443(7114):901-903, 2006.

Lubart et al., "Low Energy Laser Irradiation Promotes Cellular Redox Activity," *Photomedicine and Laser Surgery* 23(1):3-9, 2005. (15 pages).

LumiThera, "Photobiomodulation for eye diseases," Selected Abstracts, Aug. 21, 2013. (24 pages).

Masha et al., "Low-Intensity Laser Irradiation at 660 nm Stimulates Transcription of Genes Involved in the Electron Transport Chain," *Photomedicine and Laser Surgery* 31(2):47-53, 2013.

Merry et al., "Treatment of dry Age-related Macular Degeneration with Photobiomodulation," *Annual Meeting of the Association for Research in Vision and Ophthalmology*, Fort Lauderdale, FL, USA, May 6-9, 2012, 12 pages.

Moro et al., "Photobiomodulation preserves behaviour and midbrain dopaminergic cells from MPTP toxicity: evidence from two mouse strains," *BMC Neuroscience* 14:Article 40, 2013. (9 pages).

Office Action, mailed Apr. 3, 2007, for U.S. Appl. No. 11/106,416, Dotson, "Ophthalmic Phototherapy Device and Associated Treatment Method," 10 pages.

Office Action, mailed Feb. 25, 2008, for U.S. Appl. No. 11/858,351, Dotson, "Ophthalmic Phototherapy Treatment Method," 12 pages.

Office Action, mailed Jan. 14, 2015, for U.S. Appl. No. 13/679,557, Dotson et al., "Ophthalmic Phototherapy Device and Associated Treatment Method," 29 pages.

Office Action, mailed May 23, 2012, for U.S. Appl. No. 12/172,697, Dotson, "Ophthalmic Phototherapy Device and Associated Treatment Method," 31 pages.

Oron et al., "Low-level laser therapy applied transcranially to mice following traumatic brain injury significantly reduces long-term neurological deficits," *Journal of Neurotrauma* 24(4):651-656, 2007. (Abstract Only).

Purushothuman et al., "Photobiomodulation with near infrared light mitigates Alzheimer's disease-related pathology in cerebral cortex—evidence from two transgenic mouse models," *Alzheimer's Research & Therapy* 6(2), 2014. (13 pages).

Riverside Facial Plastic Surgery and Sinus Center, Gentlewaves LED Photomodulation Fact Sheet, URL=http://www.riversideface.com/pages/gentlewaves.html, download date Mar. 9, 2015. (4 pages).

Robotic LED Skin Rejuvenation, FLIP4, URL=www.medspafinancing.com/new.html, download date Mar. 1, 2005, 1 page.

Rodríguez-Santana et al., "Laser Photobiomodulation as a Potential Multi-Hallmark Therapy for Age-Related Macular Degeneration," *Photomedicine and Laser Surgery* 31(9):409-410, 2013.

Rojas et al., "Low-level light therapy of the eye and brain," *Eye and Brain* 3:49-67, 2011.

Sharma et al., "Dose Response Effects of 810 nm Laser Light on Mouse Primary Cortical Neurons," *Lasers in Surgery and Medicine* 43(8):851-859, 2011. (16 pp.).

Siletsky et al., "Time-resolved single-turnover of $ba_3$ oxidase from *Thermus thermophilus*," *Biochimica et Biophysica Acta* 1767(12):1383-1392, 2007.

Sommer et al., "Biostimulatory Windows in Low-Intensity Laser Activation: Lasers, Scanners, and NASA's Light-Emitting Diode Array System," *Journal of Clinical Laser Medicine & Surgery* 19(1):29-33, 2001.

Tang et al., "Low-Intensity Far-Red Light Inhibits Early Lesions That Contribute to Diabetic Retinopathy: In Vivo and In Vitro," *Investigative Ophthalmology & Visual Science* 54(5):3681-3690, 2013.

Tarita-Nistor et al., "Fixation Characteristics of Patients with Macular Degeneration Recorded with the MP-1 Microperimeter," *Retina* 28(1):125-133, 2008. (Abstract Only).

Tosk, "FDA Clears GentleWaves: The First and Only Light Emitting Diode Device for the Treatment of Periorbital Wrinkles and Rhytids," URL=http://www.drmcdaniel.com/fda-clears-gentlewaves, download date Mar. 9, 2015, 2 pages.

Tuchin, *Tissue Optics:Light Scattering Methods and Instruments for Medical Diagnosis*, The International Society for Optical Engineering, Bellingham, WA, USA, 2000, pp. 1-11.

(56) References Cited

OTHER PUBLICATIONS

Xuan et al., "Transcranial Low-Level Laser Therapy Improves Neurological Performance in Traumatic Brain Injury in Mice: Effect of Treatment Repetition Regimen," *PLoS One* 8(1), e53454, 2013. (9 pages).

* cited by examiner

OPHTHALMIC PHOTOTHERAPY DEVICE AND ASSOCIATED TREATMENT METHOD

CROSS-REFERENCE TO RELATED APPLICATIONS

This application is a Continuation of U.S. application Ser. No. 13/679,557, filed Nov. 16, 2012; which is a Continuation-In-Part of U.S. application Ser. No. 12/172,697, filed Jul. 14, 2008; which is a Continuation-In-Part of U.S. application Ser. No. 11/858,351, filed Sep. 20, 2007 and issued as U.S. Pat. No. 7,479,136; which is a Continuation-In-Part of U.S. application Ser. No. 11/106,416, filed Apr. 14, 2005.

STATEMENT REGARDING FEDERALLY SPONSORED RESEARCH OR DEVELOPMENT

Not Applicable

BACKGROUND OF THE INVENTION

1. Field of Invention

This invention relates to an ophthalmic phototherapy device and an associated treatment method. More specifically, the present invention is related to a device and method for exposing an eye to selected wavelengths of light to promote the healing of damaged or diseased eye tissue.

2. Description of the Related Art

Light has various uses within the medical community. Exposure of cellular tissue to light is known to modulate the activity of such cellular tissue. Different wavelengths of light act on different mechanisms within individual cells within the cellular tissue to stimulate or suppress biological activity within the cells in a process commonly referred to as photobiomodulation. In certain photobiomodulation applications, commonly known as light therapy or phototherapy, the different wavelengths are used to promote healing, revitalize and rejuvenate cells, and in some circumstances, stimulate cellular regeneration and regrowth.

Molecules like cytochrome-C oxidase, hemoglobin, myoglobin, and nicotinamide adenine dinucleotide (NADH), found in cellular tissue, are recognized as photon acceptors and serve to initiate biochemical cellular response to photons. Additionally, it is recognized that certain biologic quantum field effects result from exposing cellular tissue to photonic light and that living cells generate low levels of photons, called biophotons. These biophotons are non-thermal in nature and are coupled to physiological functions in the cellular tissue. Biophotons represent regulatory activity from chemical reactivity within a cell and also perform regulatory activity over a given cellular tissue to promote cell growth and differentiation, and to provide intercellular and intracellular communication, such as for example, synchronicity in biofunction between cells. Such biophotons within a cellular tissue can be simulated by photonic light of one or more specific wavelengths from a source external to the cellular tissue. Such photonic light, when exposed to the cellular tissue, results in promotion of regulatory activity within the cells of the exposed cellular tissue.

Thus, it is generally accepted that cell activity can be up-regulated and down-regulated by specific wavelengths of low intensity light. The up- and down-regulation of cell activity through photobiomodulation is used to suppress cytokines, block the matrix metalloproteinases (MMP) cascade, suppress interleukins (IL) and tissue necrosis factors, and decreasing inflammation of cellular tissue. Photobiomodulation is also used to affect mitochondrial density and activity, cell proliferation and adhesiveness, and DNA and RNA production. Phototherapy has been shown to affect vascular endothelial growth factor (VEGF) expression (both enhancement and suppression) and to protect against a wide variety of toxins, such as chemical, ionizing, and bacteriologic toxins.

At least some of the known effects of the various wavelengths on body tissues are as follows. Light in the yellow range (approximately 577 nm to 597 nm) has been shown to switch off collagenase production by down-regulating MMPs and switching on new collagen production. Collagenases are enzymes that break down the native collagen that holds animal tissue together. Thus, use of light in the yellow range for phototherapy ultimately results in increased cohesion of cells in animal tissue. Light in the red range (approximately 640 nm to 700 nm) has been shown to decrease inflammation in injured tissue, increase ATP production, and otherwise stimulate beneficial cellular activity. Light in the blue range (approximately 405 nm to 450 nm) has been shown to kill various microorganisms. For example, light in the blue range has been shown to kill the propionibacterium that causes acne by activating the porphyrins produced by the bacteria. Accordingly, phototherapy has been utilized to treat infants for jaundice (e.g., U.S. Pat. No. 6,811,563), to treat acne and other skin conditions (e.g., U.S. Pat. No. 6,387,089), to treat rhinitis (e.g., U.S. Pat. No. 5,683,436), and to treat traumatic tissue injuries (e.g. U.S. Pat. No. 6,471,716).

Photobiomodulation also requires the use of light with suitable intensity, energy, and wavelengths, the combination of which allows light of the selected wavelengths to penetrate the cellular tissue and activate the desired cellular mechanism without significantly causing damage to the cells. The combination of characteristics suitable for photobiomodulation applications are distinct from those of light used in other applications. Other applications use high-energy, high-intensity light sources, e.g., excimer lasers, that are destructive as opposed to regenerative, because the light emitted is so intense that, as the laser light penetrates the cellular tissue, the cells become burned, melted, or otherwise destroyed. General purpose lighting, such as an incandescent light, uses low-energy light sources ranging in intensity that is incapable of sufficiently penetrating the cellular tissue, which results in superficial exposure of the cellular tissue to the low-energy light and, therefore, reduced photobiomodulation effects. Further, an incandescent light produces numerous wavelengths and the wavelengths are not subject to independent control, which results in unpredictable modulation of the cellular activity within the exposed cellular tissue. High-intensity light of sufficient energy to properly penetrate the cellular tissue and initiate photobiomodulation tends to burn and/or melt the cellular tissue prior to the completion of a phototherapy treatment. Hence, light appropriate for use in phototherapy should exhibit both a relatively low intensity, so as not to destroy the exposed cells, and a relatively high energy, so as to allow for sufficient penetration of light into the exposed cellular tissue such that the activities of a desired portion of cells within the exposed cellular tissue are photobiomodulated.

One device which is known to produce relatively low-intensity, high-energy light suitable for use in phototherapy is the light-emitting diode (LED). Several commercial phototherapy devices are available including devices which utilize LEDs, including the Gentlewaves® LED Photomodulation Device manufactured by Light BioScience, LLC, which includes a panel of LEDs for treating skin conditions, and the Flip4 Max7 LED device which incorporates an LED panel capable of producing multiple wavelengths of light, and which is also marketed for treating skin conditions. Further, the U.S. military and NASA have utilized small hand-held devices incorporating LED arrays that are used to reduce inflammation and to promote healing in damaged skin tissue. Light from such LED devices has been shown to exhibit the low-intensity and high-energy characteristics appropriate for use in photobiomodulation.

Various laser devices have been used in the field of ophthalmology for the purposes of ablating and cutting eye tissue during laser-assisted surgery on an eye. Likewise, various laser devices have been used to melt or otherwise liquefy eye tissue surrounding a surgical wound in order to establish a weld or other such seal in the surgical wound. These destructive uses of light cause other damage to the eye tissue, but this other damage is of the type that can be healed by the body's normal recuperative mechanisms over time. In addition, a device using LEDs has been utilized in the field of ophthalmology in an effort to strengthen corneal tissue. However, this device utilizes LEDs producing wavelengths falling in the middle to far ultraviolet ranges (approximately 100 nm to 300 nm) to induce cross-linking of corneal collagen and thereby stiffen the cornea of the eye. Thus, this process, in effect, ages the corneal tissue, as opposed to facilitating the production of new, "normal" tissue. Therefore, the process is not one in which healing of eye tissue is promoted. Accordingly, none of the known phototherapy mechanisms are used for promoting the healing, regrowth, or regeneration of damaged or diseased eye tissue or for alleviating discomfort associated with damaged or diseased eye tissue within the field of ophthalmology.

BRIEF SUMMARY OF THE INVENTION

The present invention provides an ophthalmic phototherapy device, and an associated phototherapy method, for promoting healing of damaged eye tissue. The ophthalmic phototherapy device includes a light emitting mechanism for transmitting light of at least one preselected wavelength to the damaged eye tissue, whereby the light transmitted to the eye tissue stimulates activity in the eye tissue to promote healing. The light emitting mechanism can include a light panel having a plurality of light emitting diodes (LEDs) for emitting light. In one embodiment the device has a first set of LEDs capable of emitting light having a first wavelength, and at least a second set of LEDs capable of emitting light having a second wavelength. Further, a controller is provided for selectively controlling which LEDs are energized at any given time, such that different sequences and/or combinations of light wavelengths can be selectively communicated to the eye tissue being treated.

The ophthalmic phototherapy method of the present invention includes identifying a treatable portion of cellular tissue in an eye. The identified portion of damaged eye tissue is exposed to light of at least one preselected wavelength for a preselected period of time to photobiomodulate cellular activity in the cellular tissue to promote healing. Further, in one application of the method, the tissue is exposed to light of a plurality of wavelengths either sequentially, or in combination. In certain embodiments, the tissue is exposed to a continuous beam of light; in certain embodiments, the tissue is exposed to a pulsing beam of light; and in certain embodiments, the tissue is exposed to a sequential combination thereof.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
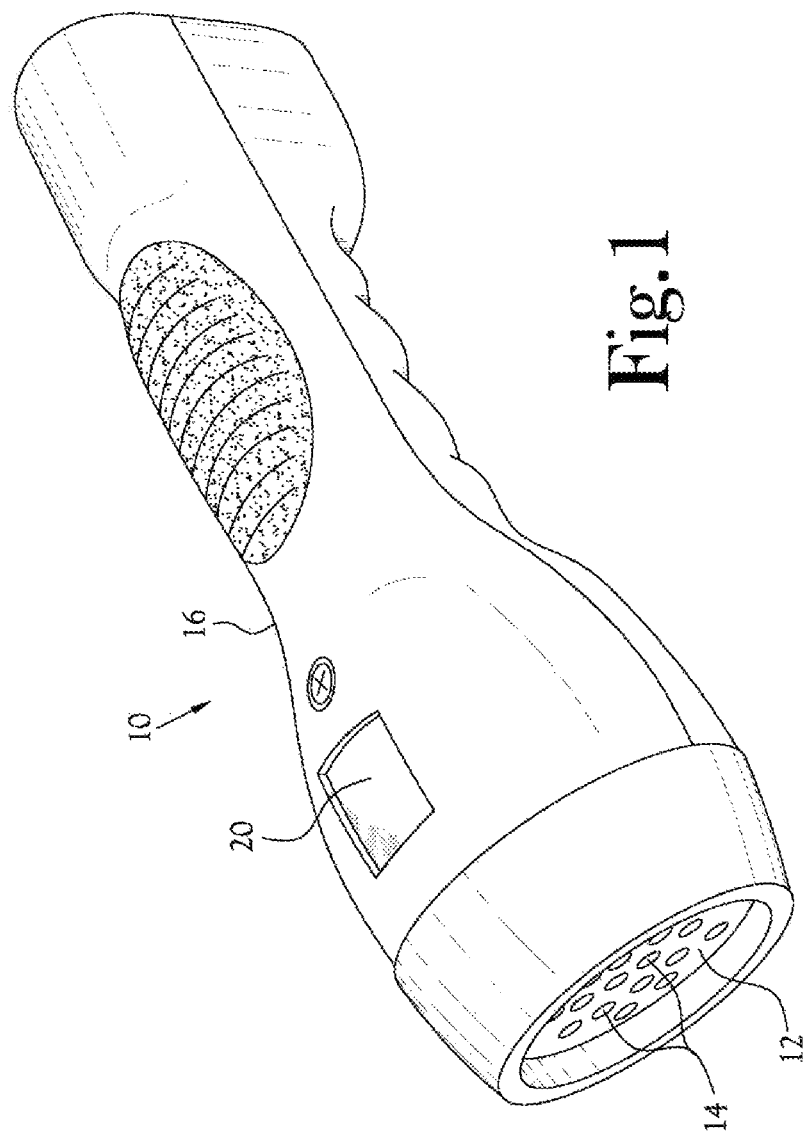
FIG. 1 is a perspective view of an ophthalmic phototherapy device constricted in accordance with several features of the present general inventive concept.

An ophthalmic phototherapy device is illustrated generally at 10 in the drawings. As will be discussed in detail below, the ophthalmic phototherapy device 10 produces light of a selected wavelength, or sequences or combinations of light having differing wavelengths within a particular range of wavelengths. In accordance with the ophthalmic treatment method of the present invention, the light emitted by the phototherapy device 10 is directed into the eye of a patient to promote healing of damaged or diseased eye tissue.

FIG. 1 illustrates one embodiment of the ophthalmic phototherapy device 10. The ophthalmic phototherapy device 10 incorporates a light emitting mechanism that includes a light panel 12 incorporating a plurality of light sources 14 that emit light having the desired wavelengths. The light panel 12 is mounted in a housing 16 that is configured to facilitate use of the device 10. A switch 20 allows the operator to control the production of light. In one embodiment, the light sources are LEDs. It will be appreciated that other mechanisms capable of emitting light of a desired wavelength, intensity, and energy can be used, and that the use of the term LEDs 14 throughout the application is not intended to limit the available mechanisms for producing the desired light. For example, the light emitting mechanism could include a low power laser source for generating light of the appropriate wavelength(s), or one or more filtered incandescent or fluorescent lights. In the illustrated embodiment, the ophthalmic phototherapy device 10 is configured for hand-held use. However, those skilled in the art will recognize that the ophthalmic phototherapy device can be either hand-held or mounted on an operatively associated medical device or other supporting structure without departing from the scope and spirit of the present invention.

Figure 2:
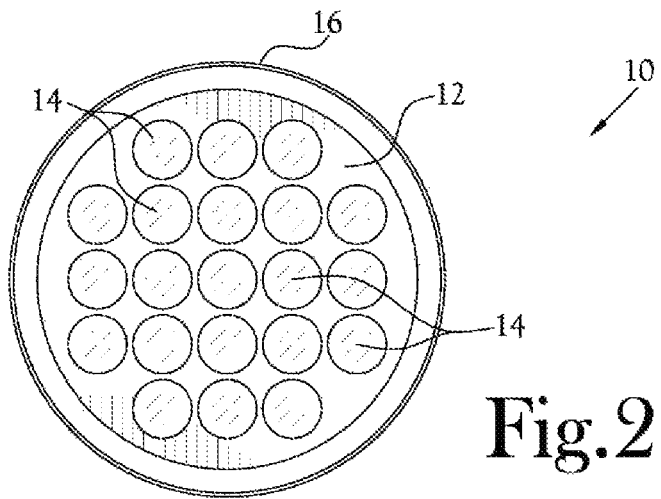
FIG. 2 is a front elevation view of an ophthalmic phototherapy device of FIG. 1.

FIG. 2 is a front elevation view of the phototherapy device 10. With respect to the particular LEDs used in the panel 12, and as will be discussed further below, one approximate range of wavelengths desirable for ophthalmic phototherapy is between 300 nm and 1000 nm. However, other wavelengths may be beneficial for certain applications. Thus, depending on the particular therapeutic application, the panel 12 can be configured to have a plurality of LEDs 14 that produce the same wavelength of light within a desired range, or the panel 12 can incorporate selected combinations of LEDs 14 capable of producing light of differing wavelengths within a desired range. As will be discussed further below, where selected combinations of LEDs 14 are used which produce different wavelengths, the operator of the device 10 can select among wavelengths to be emitted within a desired range. Alternatively, where the ability to select between the wavelengths of the light emitted is desired, the panel 12 could incorporate LEDs 14 that produce a common wavelength and conventional filters (not shown) could be used to alter the wavelength to that desired.

Figure 3:
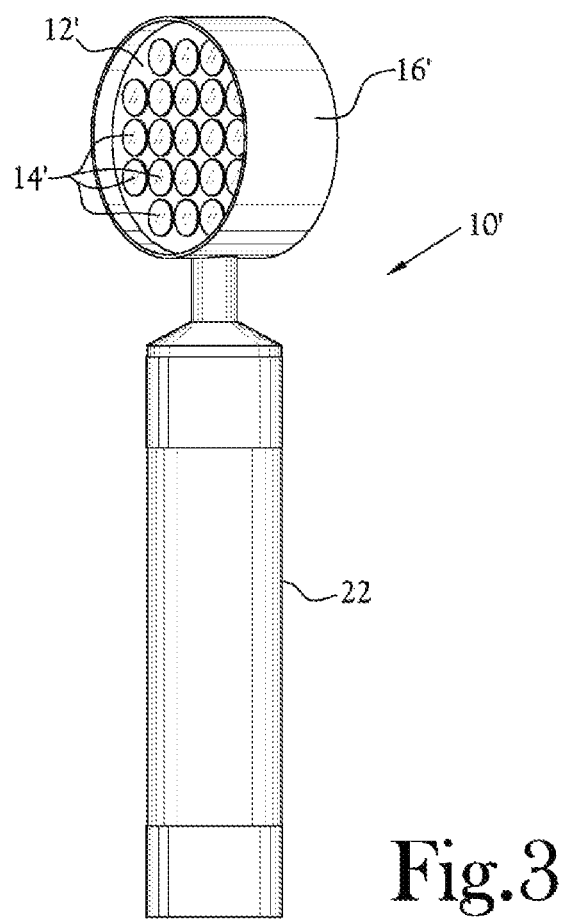
FIG. 3 is a perspective view of another embodiment of an ophthalmic phototherapy device constructed in accordance with several features of the present general inventive concept.

In FIG. 3 an alternate embodiment of the ophthalmic phototherapy device of the present invention is illustrated at 10'. It will be noted that features of the device 10' that are common to the device 10 are referenced with common prime numerals. Those skilled in the art will recognize that certain hand-held ophthalmic instruments, such as retinoscopes and ophthalmoscopes, utilize interchangeable, detachable handles which incorporate rechargeable batteries. The ophthalmic phototherapy device 10' includes a housing 16' that detachably couples with such an interchangeable, rechargeable battery handle 22. Thus, the device 10' utilizes a power supply which is commonly available to ophthalmic health care professionals, and does not require a recharging system that is unique to the phototherapy device.

Figure 4:
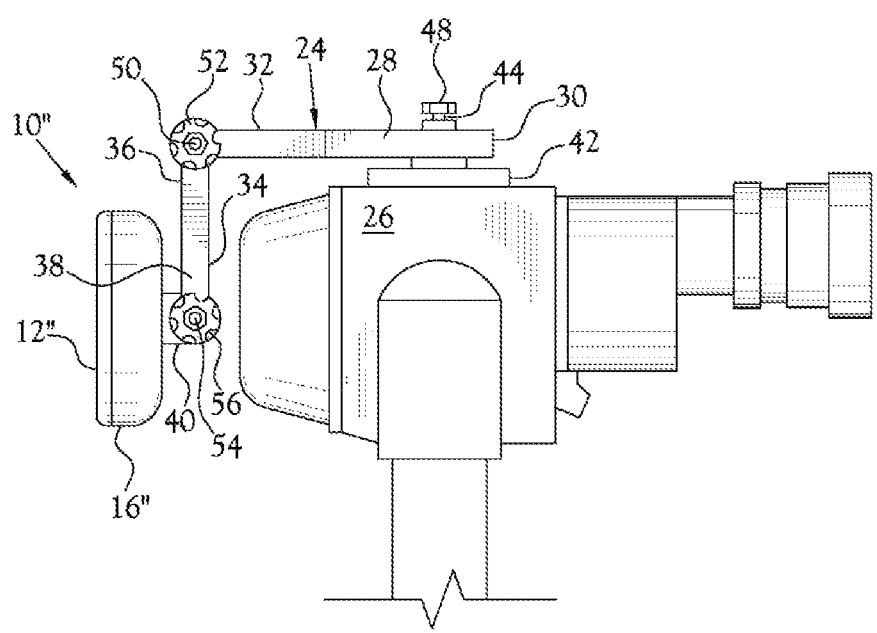
FIG. 4 is a side elevation view of another embodiment of an ophthalmic phototherapy device, showing the ophthalmic phototherapy device mounted on a slit lamp.

A further alternate embodiment of the ophthalmic phototherapy device of the present invention is illustrated at 10" in FIG. 4. In this regard, it will be noted that features of the device 10" that are common to the device 10 are referenced with common double prime numerals. As illustrated, the ophthalmic phototherapy device 10" includes an articulated arm 24 that allows the device 10" to be adjustably mounted on a piece of operatively associated ophthalmic equipment such as the illustrated slit lamp 26. Although, the device 10" is illustrated as being mounted on a slit lamp 26 in FIG. 4, it will be understood that the device 10" could be mounted on various other pieces of equipment or structures. For example, and as will be discussed further below, in one embodiment, the device 10" is mounted proximate the head of an excimer laser such that device 10" can be utilized immediately before, during and/or after laser eye surgery. In another embodiment, the device 10" is mounted proximate an ophthalmic imaging device, such as for example an optical coherence tomography (OCT) device, an autofluorescence imaging device, etc., such that the device 10" can be utilized in conjunction with the ophthalmic imaging device to deliver a phototherapy treatment to a precise area of eye tissue.

With reference to FIG. 4, whereas the articulated support arm 24 defines various jointed configurations which allow the device 10" to be selectively positioned at various locations while being supported on associated ophthalmic equipment or other structures, the illustrated arm 24 includes a first arm section 28 having first and second end portions 30 and 32, respectively. The first end portion 30 is pivotally secured to the slit lamp 26 or other supporting structure, such that the arm 24 can be selectively pivoted in a substantially horizontal plane. The second end portion 32 of the first arm section 28 is pivotally secured to the first end portion 36 of a second arm section 34 such that the second arm section 34 pivots in a substantially vertical plane. Further, the second arm section 34 is pivotally secured proximate its second end portion 38 to a bracket 40 provided on the housing 16" such that the housing 16" and the light panel 12" pivot in a substantially vertical plane which is substantially perpendicular to the plane in which the second arm section 34 pivots.

It will be recognized that various mechanisms could be used for pivotally securing the first arm section 28 to a supporting structure, for pivotally securing the first arm section 28 to the second arm section 34, and for pivotally securing the second arm section 34 to the bracket 40. However, as illustrated in FIG. 4, in one embodiment an attachment structure 42 is provided that is secured to the supporting structure, as by an adhesive or by mechanical fasteners (not shown), and a threaded fastener 44 having a locking knob 48 is used to pivotally, and lockably, secure the first end portion 30 of the first arm section 28 to the attachment structure 42. A second threaded fastener 50 having a locking knob 52 is provided for pivotally, and lockably, securing the second arm section 34 to the first arm section 28, and a third threaded fastener 54, with a locking knob 56, is provided for pivotally, and lockably, securing the second arm section 34 to the bracket 40. Thus, it will be recognized that the articulated support arm 24 allows the light panel 12" to be pivoted to a position where it does not interfere with the use of the equipment on which it is mounted, and allows the light panel 12" to be pivoted into position to emit light into the eye of a patient when needed. Whereas the ophthalmic phototherapy device 10 and device 10' could be used in conjunction with laser eye surgery, it will be recognized that use of the device 10" with its articulated support arm 24 is particularly advantageous. In this regard, the articulated support arm 24 allows the device 10" to be mounted proximate a laser surgery apparatus such that both immediately prior to and immediately following the surgical procedure, the panel 12 can be rotated into position to emit light into the eye to promote healing.

Figure 5:
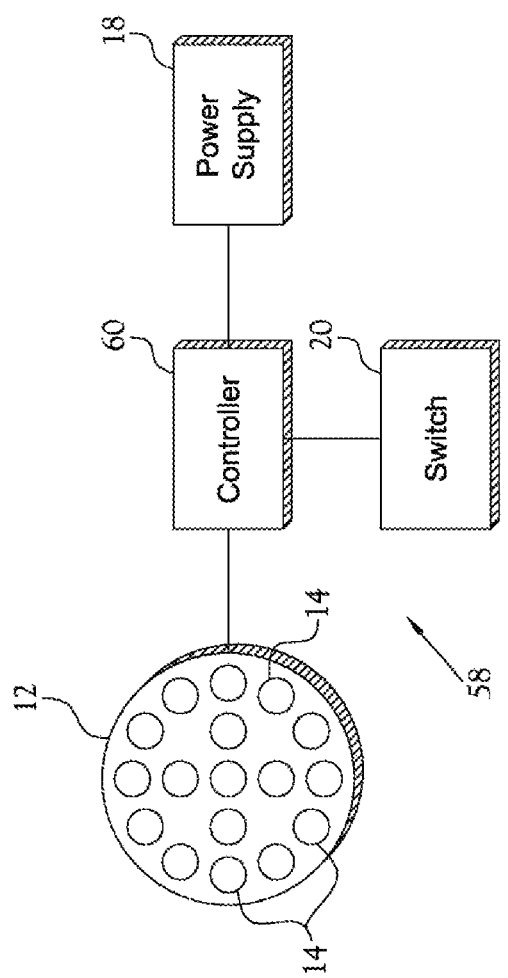
FIG. 5 is a block diagram of a power/control system for an ophthalmic phototherapy device.

FIG. 5 illustrates a block diagram of the ophthalmic phototherapy device 10. The ophthalmic phototherapy device 10 includes a power supply 18 for energizing the light panel 12 in response to operation of the switch 20 which selectively connects and disconnects the light panel 12 and the power supply 18 to turn the panel 12 on and off. In one embodiment, the power supply is a battery (not shown) that is preferably rechargeable. In other embodiments, suitable circuitry is provided for connecting the device to a conventional AC power supply such as a wall outlet. In addition, as will be discussed below with respect to the phototherapy method of the present invention, several embodiments of the ophthalmic phototherapy device 10 allow selective control of the wavelength of the light emitted by the device 10, as well as the duration of a patient's exposure to the light emitted, and the energy and intensity of the light emitted. Accordingly, the ophthalmic phototherapy device 10 illustrated in FIG. 5 includes a power/control system 58 that includes a controller 60 for activating and/or deactivating the LEDs. In several embodiments, the controller 60 includes a timer for automatically turning the LED's off after a preselected period of time. The controller 60 also controls the energy output of the LEDs 14 and the intensity of the output light, and, where LEDs 14 emitting light of different wavelengths are used, which LEDs are lit at any given time. Further, in another embodiment the controller 60 allows different LEDs to be lit in a desired sequence, or in a pulsed format. In one embodiment, the controller is implemented in discrete circuits, either analog or digital, designed to perform the various functions. In another embodiment, the controller is implemented using any processor device or other similar device providing the necessary logic and control functions.

Figure 6:
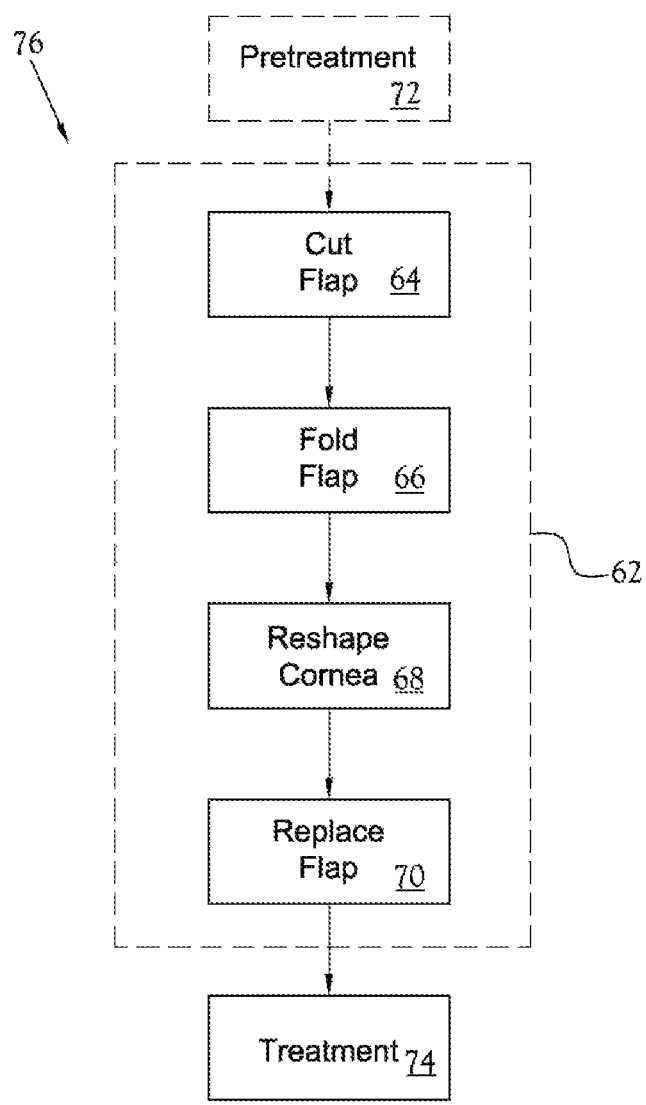
FIG. 6 is a flow diagram showing one embodiment of a method according to the present general inventive concept.

Referring to FIG. 6, the phototherapy method 76 of the present invention includes generally identifying and/or diagnosing a treatable portion of cellular tissue in an eye 62, such as a damaged and/or diseased portion of cellular tissue, or a portion of cellular tissue in which imminent damage or disease is anticipated. Once a treatable portion of cellular tissue is identified, treatment is performed 74 by directing light of at least one preselected wavelength to cells forming at least a portion of the cellular tissue to be treated. The wavelength composition of the light directed to the cellular tissue during treatment is preselected so that exposure of the cellular tissue to the light results in photobiomodulation of the cellular activity of at least a portion of the cells forming the cellular tissue, such that healing of the cellular tissue is promoted.

The approximate range of wavelengths desirable for ophthalmic phototherapy correspond to portions of the visible and invisible infrared spectrum ranging from blue light to near-infrared and infrared light, in other words, light having wavelengths between approximately 300 nm and 1000 nm, and preferably between 490 nm and 810 nm. However, both the general and preferred ranges are not intended to be limiting as wavelengths outside of these ranges may be helpful for certain treatment applications. The particular wavelength used varies depending on the injury or eye condition being treated. For example, light in the yellow range (approximately 577 nm to 597 nm) has been shown to switch off collagenase production by down-regulating MMP production and to switch on new collagen production. In the field of opthamology, yellow light having a wavelength of approximately 590 nm has been found to be beneficial for treating corneal trauma when directed into a traumatized cornea. Red light (approximately 640 nm to 700 nm) has been found to decrease inflammation of tissue in the eye, increase ATP production, and reset cellular activity to cause abnormal cells to exhibit more normal behavior. Further, a preselected sequence or combination of wavelengths can be advantageously used in certain conditions. For example, a sequence or combination of infrared or near-infrared light, red light, and yellow light directed into the eye at a dosage of approximately 4 joules/sq. cm has been found to be beneficial for treating glaucoma. Similar dosages of sequences or combinations of infrared or near-infrared light, red light, and yellow light have been found to stimulate the cells in the trabecular meshwork to produce macrophages that then reduce the pigment cells clogging the meshwork of the eye, thereby allowing the eye to drain.

The duration of the phototherapy treatments varies depending on the particular eye condition being treated. Beneficial tissue response can be obtained from dosages of less than 4 joules/sq. cm, such that the duration of treatment can be relatively short. Exposure times of less than one minute can be beneficial, with exposure times in excess of 10 minutes being contemplated. For example, to achieve approximate dosages of less than 4 joules/sq. cm, treatment duration could vary between under a minute to approximately 10 minutes, depending upon the output power and intensity of the light source utilized. Further, although phototherapy treatments of less than 0.1 joules/sq. cm, and having durations of 40 seconds or less, have been shown to be beneficial, longer treatments may be desirable to provide additional benefit, or to allow for larger dosages of light energy per unit area of cellular tissue. Of course, it will be understood by one skilled in the art that beneficial tissue response can be obtained from dosages of light energy greater than 4 joules/sq. cm, and such dosages may be used without departing from the spirit and scope of the present invention.

FIG. 6 is a block diagram of one method 76 for promoting healing of eye tissue. In the illustrated embodiment, the method begins with a wavelength selection step 78, involving the selection of one or more wavelengths of light for use in the method 76. As discussed above, the particular wavelengths selected for use depends upon the desired cellular activity to be stimulated through application of the method 76. For example, in one embodiment, wavelengths in the red and near-infrared spectrums are selected to suppress inflammation of the eye tissue. In another embodiment, wavelengths in the yellow spectrum are selected to suppress collagenase production and to stimulate new collagen production. In still another embodiment, wavelengths in multiple color spectrums are selected to stimulate multiple desired cellular activities in the treated eye tissue.

In a dosage selection step 80, a suitable dosage of light is selected for use in the method 76 for the selected wavelength. In the illustrated embodiment, selection of the dosage 80 includes selection of amount of light energy 82 to be delivered over a selected period of time 84 at a selected intensity 86. However, it will be understood that other factors, such as for example the topical area of cellular tissue to be treated, diffusion of the light to be applied, and other such factors, may be selected during the selection of dosage 80 without departing from the spirit and scope of the present invention. A light source is provided which is capable of generating a beam of light having the characteristics selected during the dosage selection step 80. At a treatment phase 74, the light source is used to generate a beam of light 88 having the characteristics selected during the dosage selection step 80. In the illustrated embodiment, a beam of light is generated 88 having the energy, duration, and intensity characteristics selected in the dosage selection step 80. Of course, it will be understood that the particular characteristics of the generated beam of light depend upon the specific factors selected during the dosage selection step 80. At a direction step 90, the beam of light 88 is directed to a portion of eye tissue to be treated. Upon exposure of cells in the eye tissue to the beam of light 88, at least a portion of the cells are stimulated to undergo at least one desired cellular activity corresponding to the selected wavelength. In this way, cellular activity useful in promotion of healing of the eye tissue is stimulated.

Figure 7:
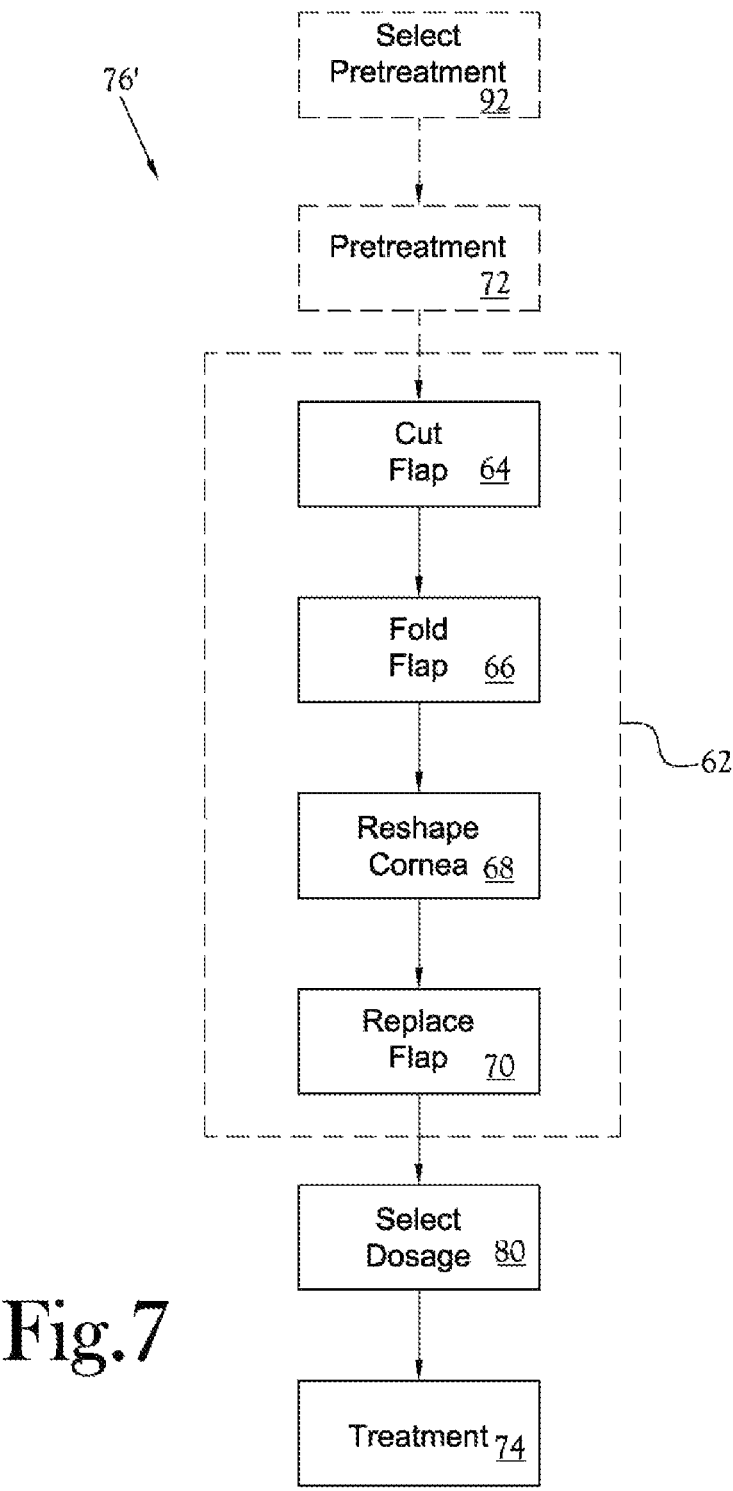
FIG. 7 is a flow diagram showing another embodiment of the method of the present general inventive concept.

In another embodiment, illustrated in FIG. 7, the method 76' is used for promoting healing of eye tissue both before and after performing a medical procedure on the eye to correct vision problems. In the illustrated embodiment, the method begins with an optional pretreatment dosage selection step 92, wherein a dosage is selected for an optional pretreatment step 72. The pretreatment step 72 involves directing light of one or more selected wavelengths of selected energy, duration, and intensity characteristics into the cornea of the patient's eye in order to stimulate the eye tissue to engage in cellular activity beneficial to healing. In one embodiment, the light uses wavelengths in the red and near-infrared spectrums to suppress inflammation of the eye tissue during and after surgery. In another embodiment, the light used in the pretreatment step 72 uses wavelengths in both the yellow and red spectrums to suppress inflammation of the eye tissue during and after surgery, to suppress collagenase production, and to stimulate new collagen production.

In a damage phase 62, a medical procedure for correcting vision problems is performed, thereby damaging a portion of eye tissue. The medical procedure of the illustrated embodiment uses laser surgery of the epithelium and stroma portions of the cornea of the eye, a laser-assisted in situ keratomilcusis procedure commonly referred to as LASIK eye surgery as an example. The LASIK procedure involves the step 64 of cutting a flap in the epithelium of the cornea of an eye while leaving the eye tissue at one end of the flap uncut. It will be appreciated by those familiar with LASIK that a knife, referred to as a microkeratome, or a laser, such as the IntraLase™ femtosccond (1054 nm) laser, can be used to cut the flap 64. In a folding step 66, the uncut tissue serves as a hinge that allows the flap to be folded back to reveal the stroma, or middle section of the cornea. A reshaping step 68 uses pulses from a computer controlled excimer laser to vaporize a portion of the stroma and reshape the cornea. The LASIK procedure ends with a flap replacement step 70 in which the flap of epithelium tissue is replaced 70.

To this extent, in the illustrated embodiment, the damage phase 62 includes performing LASIK eye surgery on an eye. However, while the embodiment of the method in FIG. 7 illustrates the performance of laser eye surgery at the damage phase 62, it will be understood that the phototherapy method of the present invention can also be beneficially used to promote healing of eye tissue in connection with various other eye conditions. For example, the method 76' is also effective in promoting healing in connection with LASIK or Epi-Lasik procedures, corneal inlays, corneal transplants (penetrating keratoplasty or PKP), cataract and intraocular implant (IOL) surgery, and glaucoma surgery. Utilized during or after such procedures, the present phototherapy method reduces healing time and the need for extended use of postoperative drugs such as steroids. Moreover, the phototherapy method of the present invention is useful in promoting healing of damaged eye tissue whether the damage is the result of disease, accident, surgery, or other such occurrences. To this extent, in another embodiment, the damage phase 62 is accomplished by allowing a portion of cellular tissue in an eye to become damaged or diseased.

Following the damage phase 62, a treatment dosage selection step 80 is performed. As discussed above, selection of the treatment dosage 80 includes selection of an amount of light energy to be delivered over a selected period of time at a selected intensity. In a treatment step 74, light of a selected wavelength is directed into the cornea of the patient's eye in accordance with the selected treatment dosage 80 for photobiomodulating the damaged eye tissue to promote healing and suppress inflammation.

Whereas numerous wavelengths are beneficial during the optional initial step 72, the yellow range of wavelengths (approximately 577 nm to 597 nm) is particularly beneficial for treatment 74 of the eye tissue after laser eye surgery. Thus, in one embodiment, the light directed into the patient's eye 72 subsequent to replacement of the epithelial flap 70 is preselected to exhibit a wavelength in the yellow spectrum, having a range of approximately 577 nm and 597 nm. In another embodiment, the light directed into the patient's eye 72 subsequent to replacement of the epithelial flap 70 is preselected to exhibit a wavelength between the range of approximately 577 nm and 1000 nm. In more discreet embodiments, the light directed into the patient's eye 72 following laser surgery 62 is preselected to exhibit multiple wavelengths in the yellow light spectrum, having ranges of between approximately 577 nm to 597 nm, and the red and near-infrared spectrum, having ranges between approximately 640 nm to 1000 nm.

In another embodiment, illustrated in FIG. 8, the method 76" is used for promoting healing of retinal eye tissue exhibiting age-related macular degeneration (ARMD), and in particular, the so-called "dry form" of ARMD (hereinafter "dry ARMD"). In the illustrated embodiment, the method 76" begins with an initial diagnosis step 94 wherein a condition of dry ARMD is diagnosed in a patient. In several embodiments, the diagnosis step 94 is performed either through a vision test of the type known in the art, through visual examination of the patient's eye, or both. However, in certain more discreet embodiments, the diagnosis step 94 is performed using an ophthalmic imaging technique, such as for example by performing fluorescein angiography of the retina of the patient, or through use of an ophthalmic imaging device. In certain embodiments, an optical coherence tomography (OCT) device of the type known to one of skill in the art is used. More specifically and with reference to FIG. 9, in the illustrated embodiment, an OCT device is used to direct a measure of light 96 to a retina of a patient's eye. Thereafter, the OCT device detects 98 the degree to which the directed light is scattered through eye tissue in the patient's eye, and such data is used to generate 100 a high-resolution image of the patient's retinal eye tissue. Thereafter, the image of the patient's retinal eye tissue is examined 102, whereupon the presence of dry ARMD is confirmed, thereby diagnosing 94 the patient with dry ARMD.

Figure 8:
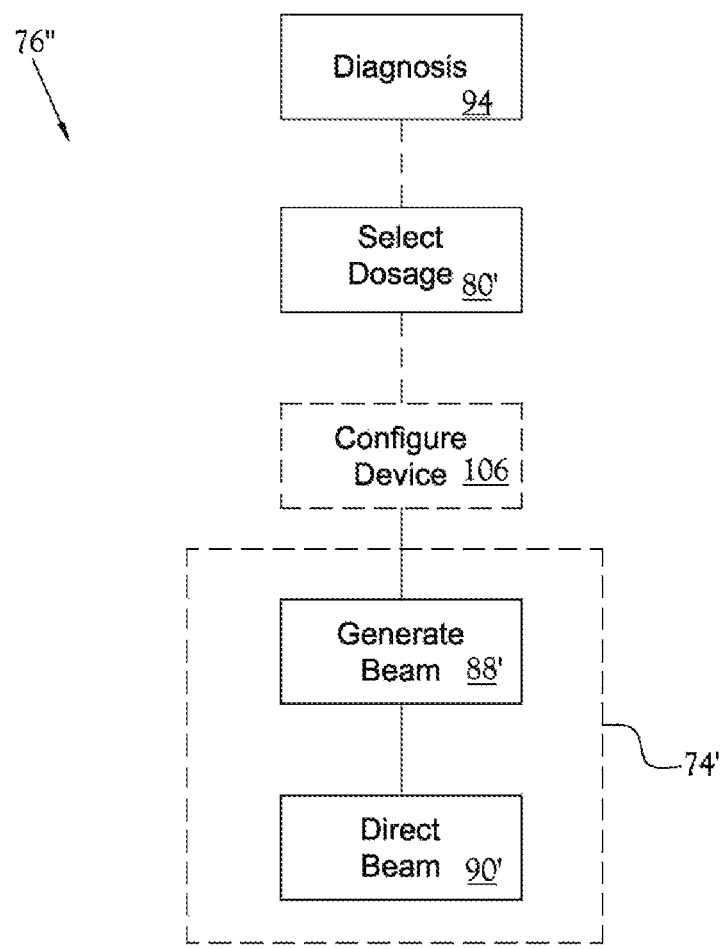
FIG. 8 is a flow diagram showing another embodiment of the method of the present general inventive concept.
Figure 9:
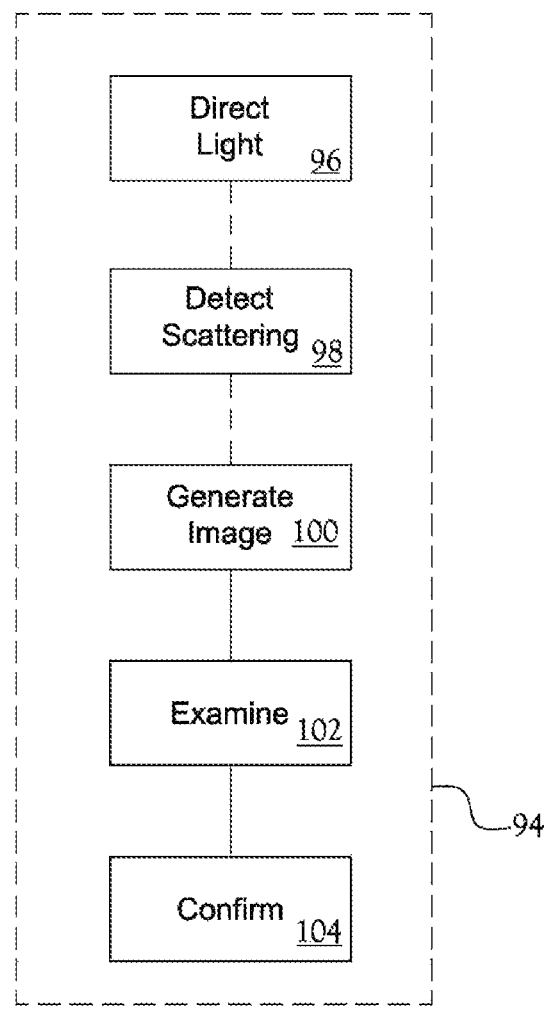
FIG. 9 is a flow diagram showing several additional operations associated with the diagnosis operation of the method shown in FIG. 8.

Upon diagnosis 94 of dry ARMD in a patient's eye, a treatment dosage selection step 80' is performed as shown in FIG. 8. As discussed above, selection of the treatment dosage 80' includes selection of an amount of light energy having one or more wavelengths to be delivered over a selected period of time at a selected intensity. Once the treatment dosage is selected 80', in an optional step, an ophthalmic phototherapy device 10 of the type discussed above may be configured 106 to generate at least one beam of light conforming to the selected treatment dosage. Alternatively, an ophthalmic phototherapy device 10 may be provided which is pre-configured to deliver the selected treatment dosage. In a subsequent treatment step 74', light of the selected wavelength or wavelengths is generated 88' and then directed 90' into the retina of the patient's eye in accordance with the selected treatment dosage 80' for photobiomodulating the retinal eye tissue to promote recovery of the retinal eye tissue from the effects of dry ARMD.

It will be understood that the exact intensity, energy, and duration of light which must be generated 88' and directed 90' at the patient's eye in order to deliver the selected dosage to the patient's retinal eye tissue is dependent, among other factors, upon the amount of, and transparency or opaqueness of, any matter imposed between the ophthalmic phototherapy device 10 and the retinal tissue to be treated. For example, in certain embodiments in which the patient's eyelid is to remain closed during treatment 74', light that is generated 88' and directed 90' toward the patient's eye is of much higher intensity and energy than that which is needed to accomplish the selected dosage. Thus, it is understood that the light will first pass through the closed eyelid of the patient before reaching the patient's retinal eye tissue, whereupon only a portion of the generated 88' and directed 90' light will reach the patient's retinal eye tissue, thereby accomplishing delivery of the selected dosage to the retinal eye tissue. In other embodiments, the patient's eyelid is to remain open during treatment 74'. In these embodiments, light that is generated 88' and directed 90' toward the patient's eye is of only slightly higher intensity and energy than that which is needed to accomplish the selected dosage. Thus, it is understood that the light will pass through the relatively transparent cornea, lens, and vitreous humor of the eye without losing much of its intensity and energy, whereupon most of the generated 88' and directed 90' light will reach the patient's retinal eye tissue, thereby accomplishing delivery of the selected dosage to the retinal eye tissue.

Figure 10:
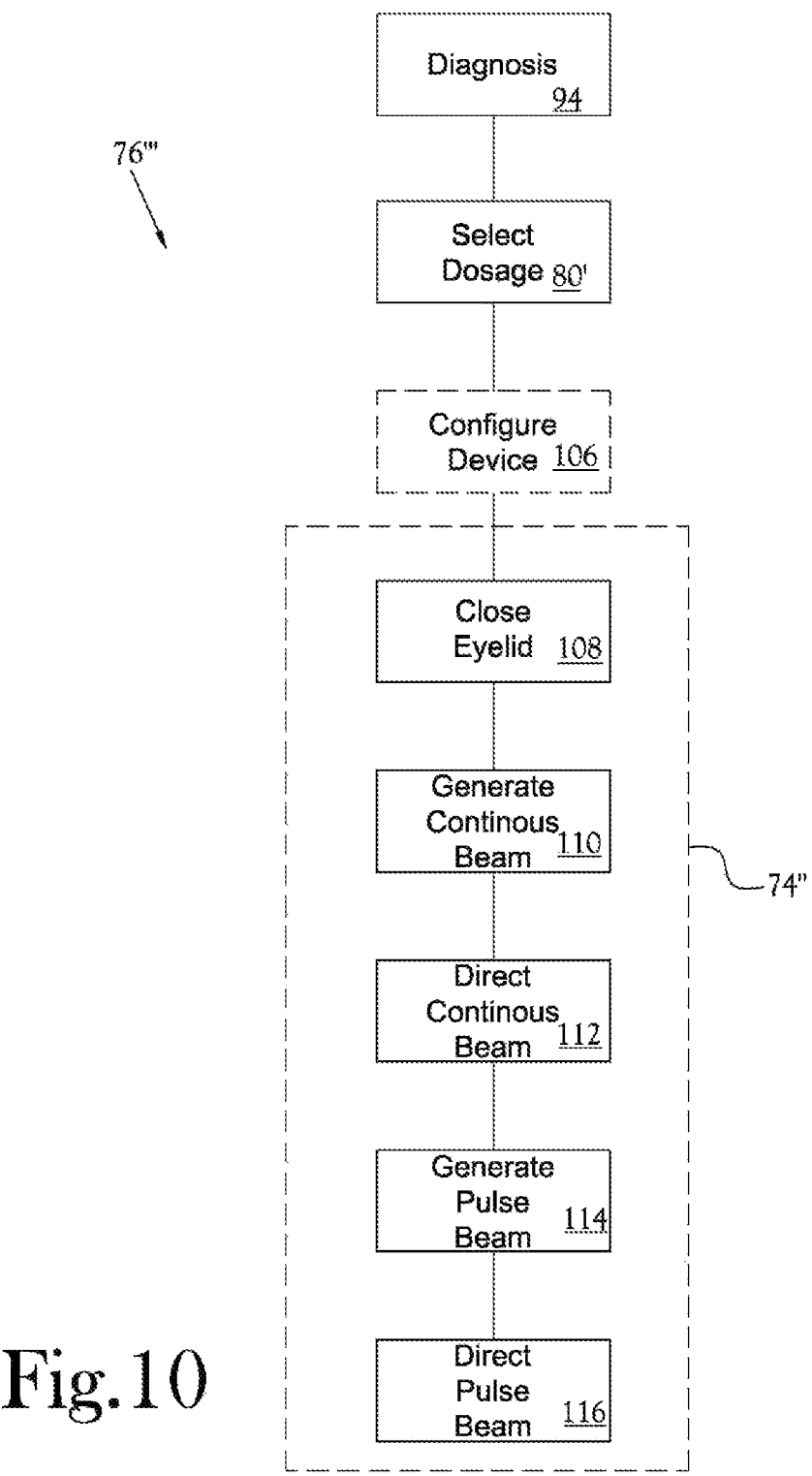
FIG. 10 is a flow diagram showing another embodiment of the method of the present general inventive concept.

Numerous selectable dosages of light phototherapy have been found to be beneficial in the treatment 74' of dry ARMD. In one embodiment, the selected treatment dosage comprises a plurality of different light beams applied in sequence to the patient's retinal tissue. For example, in the embodiment illustrated in FIG. 10, a method 76''' is shown in which the treatment step 74" includes ensuring 108 that the eyelid of the patient's eye to be treated is closed. A continuous beam of light is first generated 110 exhibiting a wavelength between approximately 580 nm to 680 nm, and preferably approximately 670 nm. This generated continuous beam is then directed 112 to the retinal tissue of the patient's eye through the patient's closed eyelid for approximately 80 to 90 seconds to achieve an initial applied dose of approximately 4 joules/sq. cm. to the patient's eyelid, with the effective dose reaching the patient's retinal tissue through the closed eyelid and other interposed eye tissue being approximately 0.4 joules/sq. cm.

Following the application 112 of the continuous beam to the patient's retina, a pulsing beam of light is generated 114. The generated pulsing beam, in several embodiments, exhibits multiple wavelengths in the red and/or near-infrared spectrum, and exhibits a pulse rate, or duty cycle, in which the beam is turned on and off at predetermined intervals. In several embodiments, the duty cycle of the pulsing beam, that is, the ratio of duration that the pulsing beam is "on" versus the duration that it is "off," is between approximately 30% "on" and 70% "off," and approximately 70% "on" and 30% "off." For example, in one embodiment, a pulsing beam is generated 114 exhibiting at least a first wavelength between approximately 580 nm to 680 nm, and preferably approximately 670 nm, as well as at least a second wavelength between approximately 850 nm to 950 nm. In this embodiment, the pulsing beam exhibits a duty cycle of approximately 250 milliseconds on and 150 milliseconds off. The generated pulsing beam is directed 116 to the retinal tissue of the patient's eye through the patient's closed eyelid for approximately 35 to 45 seconds, or approximately 100 cycles, to achieve an initial applied dose of approximately 0.11 joules/sq. cm. to the patient's eyelid, with the effective dose reaching the patient's retinal tissue through the closed eyelid and other interposed eye tissue being approximately 0.01 joules/sq. cm.

It will be understood that, while the above-discussed dosage of light phototherapy has been found to be beneficial in the promotion of healing in retinal tissue demonstrating dry ARMD, it is in no way the intention of the applicant to limit the scope of the present general inventive concept to the above-discussed ranges of wavelengths and/or duty cycles. For example, in certain embodiments, a dosage is selected 80' and applied in the treatment step 74' in which the pulsing beam exhibits a duty cycle of approximately 50% "on" and 50% "off." In certain embodiments, the various wavelengths of the pulsing beam may include two or more wavelengths in the red spectrum and/or two or more wavelengths in the near-infrared spectrum. Furthermore, in certain embodiments, multiple ophthalmic phototherapy devices 10 may be provided to produce the various wavelengths of light comprising a given selected dosage, such that each discreet wavelength emanates from a separate ophthalmic phototherapy device, rather than a light phototherapy dosage comprising a plurality of collimated wavelengths emanating from a single ophthalmic phototherapy device 10. Moreover, as discussed above, the specific energy and/or intensity of light used in the treatment step 74' may be adjusted to accommodate either an open or closed eyelid of a patient, and it is not the intention of the applicant to limit the scope of the present general inventive concept to methods which necessarily require opening or closure of the patients eyelid for treatment.

In light of the above, it will be recognized that the ophthalmic phototherapy devices 10, 10', and 10" are particularly well suited for administering phototherapy to the eye of a patient. It will be noted that use of the ophthalmic phototherapy device 10", with its articulated support arm 24 (see FIG. 4), can be particularly useful in applying phototherapy in accordance with the present method 76' subsequent to laser eye surgery 62. In this regard, the articulated support arm 24 allows the panel 12" to be rotated into position to emit light into the patient's eye immediately upon completion of the surgical procedure.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, what is claimed is:

1. A method for treating inflammatory eye disease inside an eye of a patient, said method comprising:
   during a treatment session with a phototherapy device having one or more arrays of LED(s), low power laser source(s), or any combination thereof, directing, for a first preselected period of time, a first light of at least a first wavelength into the eye of the patient to expose at least a portion of an affected eye tissue inside the eye to said first light, wherein said first light has a first preselected brightness; and
   during the treatment session, directing, for a second preselected period of time, a second light of at least a second wavelength into the eye of the patient to expose said portion of said affected eye tissue to said second light, wherein said second light has a second preselected brightness, wherein said first wavelength is different from said second wavelength, and further wherein said first and second wavelengths are selected from wavelengths of light corresponding to near infrared, yellow and red light.

2. The method of claim 1, wherein said first and second lights are directed into the eye of the patient in a manner comprising at least one of sequentially or in combination or in a pulsed format.

3. The method of claim 1, wherein said first and second lights are directed into the eye sequentially and wherein the first preselected period of time is different than said second preselected period of time.

4. The method of claim 1, wherein said first and second lights are directed into the eye in combination and said first and second preselected periods of time are the same.

5. The method of claim 1, wherein said first wavelength is within the range of approximately 577 to 597 nm and the second wavelength is within the range of approximately 640 nm to 700 nm.

6. The method of claim 1, wherein said first wavelength consists of red or yellow light and said second wavelength consists of near infra-red light.

7. The method of claim 1, further comprising, during the treatment session, exposing said portion of said eye tissue to a third light of at least a third wavelength for a third preselected period of time, said third light having a third preselected brightness, wherein said third wavelength is different from said first and second wavelengths.

8. The method of claim 7, wherein said first, second and third lights are directed into the eye of the patient in a manner comprising at least one of sequentially or in combination or in a pulsed format.

9. The method of claim 7, wherein said first, second and third lights are directed into the eye sequentially and wherein the first preselected period of time is different than said second and third preselected periods of time.

10. The method of claim 7, wherein said first, second and third lights are directed into the eye in combination and said first, second and third preselected periods of time are the same.

11. The method of claim 7, wherein each of said first, second and third wavelengths are selected from wavelengths of light corresponding to near infra-red, yellow and red light.

12. The method of claim 7 wherein one of the first, second and third wavelengths is between approximately 577 nm and 597 nm, and wherein another of the first, second and third wavelengths is between approximately 640 nm and 700 nm.

13. The method of claim 1, wherein said first and second lights are each produced by said one or more arrays of LED(s), low power laser source(s), or a combination thereof.

14. The method of claim 7, wherein said first, second and third lights are each produced by said one or more arrays of LED(s), low power laser source(s), or a combination thereof.

15. A method for treating diseased eye tissue of a patient having an inflammatory eye disease, said method comprising:
during a treatment session with a phototherapy device having one or more arrays of LED(s), low power laser source(s), or any combination thereof, exposing said diseased eye tissue to a first light of at least a first wavelength between approximately 490 nm and 810 nm for a first preselected period of time, said first light having a first preselected brightness; and
during the treatment session, exposing said diseased eye tissue to a second light of at least a second wavelength for a second preselected period of time, said second light having a second preselected brightness, wherein said first wavelength is different from said second wavelength.

16. The method of claim 15, wherein said first and second lights are directed into the eye of the patient in a manner comprising at least one of sequentially or in combination or in a pulsed format.

17. The method of claim 15, wherein said first and second lights are directed into the eye sequentially and wherein the first preselected period of time is different than said second preselected period of time.

18. The method of claim 15, wherein said first and second lights are directed into the eye in combination and said first and second preselected periods of time are the same.

19. The method of claim 15, wherein said second light consists of near infra-red light.

20. The method of claim 15, wherein said first light consists of red or yellow light and said second wavelength consists of near infra-red light.

21. The method of claim 15, wherein said first light consists of red light and said second light consists of yellow light.

22. The method of claim 15, wherein said first light consists of a combination of red and yellow light, and said second light consists of near infra-red light.

23. The method of claim 15, further comprising, during the treatment session, exposing said eye tissue to a third light of at least a third wavelength for a third preselected period of time, said third light having a third preselected brightness, wherein said third wavelength is different from said first and second wavelengths.

24. The method of claim 23, wherein said first, second and third lights are directed into the eye of the patient in a manner comprising at least one of sequentially or in combination or in a pulsed format.

25. The method of claim 23, wherein each of said first, second and third lights are selected from near infra-red, yellow and red light.

26. The method of claim 23, wherein said first, second and third lights are each produced by said one or more arrays of LED(s), low power laser source(s), or a combination thereof.

27. A method for treating diseased eye tissue inside an eye of a patient having an inflammatory eye disease, said method comprising:
during a treatment session with a phototherapy device having one or more arrays of LED(s), low power laser source(s), or any combination thereof, directing, for a first preselected period of time, a first light of at least a first wavelength into the eye of the patient to expose at least a portion of said diseased eye tissue to said first light, wherein said first light has a first preselected brightness;
during the treatment session, directing, for a second preselected period of time, a second light of at least a second wavelength into the eye of the patient to expose said portion of said diseased eye tissue to said second light, wherein said second light has a second preselected brightness; and
during the treatment session, directing, for a third preselected period of time, a third light of at least a third wavelength into the eye of the patient to expose said portion of said diseased eye tissue to said third light, wherein said third light has a third preselected brightness, and
further wherein each of said first, second and third wavelengths are selected from wavelengths of light corresponding to near infra-red, yellow and red light.

28. The method of claim 27, wherein said first, second and third lights are directed into the eye of the patient in a manner comprising at least one of sequentially or in combination or in a pulsed format.

29. The method of claim 27, wherein said first, second and third lights are directed into the eye sequentially and wherein the first, second and third preselected periods of time are each different from one another.

30. The method of claim 27, wherein said first, second and third lights are directed into the eye in combination and said first, second and third periods of time are the same.

31. The method of claim 27, wherein said first wavelength is within the range of approximately 577 to 597 nm and the second wavelength is within the range of approximately 640 nm to 700 nm.

32. The method of claim 27, wherein said first, second and third lights are each produced by said one or more arrays of LED(s), low power laser source(s), or a combination thereof.

\* \* \* \* \*

UNITED STATES PATENT AND TRADEMARK OFFICE
CERTIFICATE OF CORRECTION

PATENT NO. : 9,592,405 B2
APPLICATION NO. : 15/050483
DATED : March 14, 2017
INVENTOR(S) : Robert S. Dotson Page 1 of 1

It is certified that error appears in the above-identified patent and that said Letters Patent is hereby corrected as shown below:

On the Title Page

Item (72)
"Graham Merry, Toronto (CA)" should be removed from the patent.

Item (56)
"Fells et al., "Mitochondrial signal transduction in accelerated wound and retinal healing by near-infrared light therapy," *Mitochondrion* 4(5-6):559-567, 2004." should read, --Eells et al., "Mitochondrial signal transduction in accelerated wound and retinal healing by near-infrared light therapy," *Mitochondrion* 4(5-6):559-567, 2004.--.

Signed and Sealed this
Twenty-third Day of May, 2017

Michelle K. Lee
*Director of the United States Patent and Trademark Office*